(12) United States Patent
Brodkin et al.

(10) Patent No.: US 6,761,760 B2
(45) Date of Patent: *Jul. 13, 2004

(54) DENTAL PORCELAINS

(75) Inventors: Dmitri Brodkin, West Orange, NJ (US); Carlino Panzera, Hillsborough, NJ (US); Paul Panzera, Mt. Holly, NJ (US)

(73) Assignee: Pentron Corporation, Wallingford, CT (US)

(*) Notice: Subject to any disclaimer, the term of this patent is extended or adjusted under 35 U.S.C. 154(b) by 14 days.

This patent is subject to a terminal disclaimer.

(21) Appl. No.: 10/171,278

(22) Filed: Jun. 12, 2002

(65) Prior Publication Data

US 2003/0122270 A1 Jul. 3, 2003

Related U.S. Application Data

(63) Continuation-in-part of application No. 09/608,587, filed on Jun. 29, 2000, now Pat. No. 6,428,614.
(60) Provisional application No. 60/142,204, filed on Jul. 2, 1999.

(51) Int. Cl.[7] .......................... A61C 13/083; C03C 8/02; C03C 12/00; C03C 10/10
(52) U.S. Cl. .......................... 106/35; 501/14; 501/11; 501/17; 501/18; 264/16; 264/19; 264/20; 433/202.1; 433/203.1; 433/201.1; 433/212.1
(58) Field of Search .......................... 501/14, 11, 17, 501/18; 106/35; 264/16, 19, 20; 433/202.1, 203.1, 201.1, 212.1

(56) References Cited

U.S. PATENT DOCUMENTS

| | | | |
|---|---|---|---|
| 5,308,391 A | * | 5/1994 | Komma et al. ............... 106/35 |
| 5,453,290 A | | 9/1995 | Van Der Zel |
| 5,653,791 A | | 8/1997 | Panzera et al. |
| 6,120,591 A | * | 9/2000 | Brodkin et al. ............... 106/35 |
| 6,428,614 B1 | * | 8/2002 | Brodkin et al. ............... 106/35 |

FOREIGN PATENT DOCUMENTS

| | | |
|---|---|---|
| CA | 2070691 | 12/1992 |
| EP | 0 272 745 | 12/1987 |
| EP | 0 518 454 A2 | 5/1992 |
| EP | 0 870 479 A2 | 10/1998 |
| WO | WO 95/11866 | 5/1995 |
| WO | WO 99/18910 | 4/1999 |

OTHER PUBLICATIONS

PCT International Search Report with mail date of Nov. 20, 2000.
International Preliminary Examination Report with mail date of Oct. 22, 2001.
PCT Written Opinion with mail date of Jul. 26, 2001.
"Clay and Vocabulary Concepts." [http://scitech.stisd.net/minkc/clayterms.html]. Jan. 15, 2002.
Perkins, W., Ceramic Glossary, 1984, The American Ceramic Society, pp. 33 & 52.
Skinner, E. W., Phillips, R. W., The Science of Dental Materials, W.B. Saunders Company, 1980, pp. 270 & 271.

* cited by examiner

*Primary Examiner*—C. Melissa Koslow
(74) *Attorney, Agent, or Firm*—Ann M. Knab

(57) ABSTRACT

Opaque porcelains for use with metal cores in the manufacture of PFM restorations. The porcelains exhibit a coefficient of thermal expansion (CTE) substantially equal to or slightly above the CTE of the metal to which it is applied. The porcelains exhibit a CTE equal to or up to about $1.5 \times 10^{-6}/°C$. higher than the dental alloys to which they are applied as the opaque. The porcelains are fabricated from a mixture of two frit compositions. A high expansion, leucite containing frit is combined with a low melting glass frit to provide a porcelain having an expansion in the range of 16.9 to about $18.5 \times 10^{-6}/°C$. in the temperature range of $250°–600°$ C.

23 Claims, 1 Drawing Sheet

DENTAL PORCELAINS

CROSS-REFERENCE TO RELATED APPLICATIONS

This application is a continuation-in-part of application Ser. No. 09/608,587 filed Jun. 29, 2000, now U.S. Pat. No. 6,428,614, which claims priority to provisional application Ser. No. 60/142,204 filed Jul. 2, 1999, both which are hereby incorporated by reference.

FIELD OF THE INVENTION

This invention relates to low fusing high-expansion dental porcelain especially useful for the fabrication of both all-ceramic and porcelain-fused-to-metal (PFM) restorations.

BACKGROUND OF THE INVENTION

Porcelains are typically designed to be used in the manufacture of either all-ceramic dental restorations or in PFM restorations, but are not normally functional with both types of restorations due to the differences in properties of ceramics and metals. One such porcelain, OPC® Low Wear™ porcelain, available from Jeneric/Pentron Inc., Wallingford, Conn. and covered in copending, commonly assigned patent application Ser. No. 09/133,582 filed Aug. 13, 1998, now U.S. Pat. No. 6,120,591, which is hereby incorporated by reference, was initially designed to be used as overlay for pressed all-ceramic restorations as well as for the fabrication of porcelain jacket crowns and veneers. However, OPC® Low Wear™ porcelain is not currently used for PFM restorations despite its wear resistance, forgiveness to natural dentition and strength being superior to those of conventional PFM porcelains as shown in the Table 1 below:

TABLE 1

| Property | OPC ® Low Wear ™ Porcelain | Conventional Porcelain for PFM |
| --- | --- | --- |
| Leucite average grain Size, μm | About 2–3 | About 5–8 |
| Leucite volume fraction, % | 35–40 | 20–25 |
| Enamel wear, ×10$^{-2}$ mm$^2$ | 7.69 ± 3.20 | 18.23 ± 5.20 |
| Wear of ceramics, ×10$^{-2}$ mm$^3$ | 0.16 ± 0.04 | 0.49 ± 0.11 |
| CTE, 10$^{-6}$/° C., 25° C.–500° C. | About 17 | About 13 |

The major obstacle preventing use of the OPC® Low Wear™ porcelain in PFM restorations is the absence of an opaque/alloy combination compatible with this porcelain having relatively high expansion of about 17×10$^{-6}$/° C. (25° C.–500° C.).

There exists a Golden Gate System™ for PFM restorations available through Degussa™ (Dental Division, South Plainfield, N.J.) which combines Duceragold™ porcelain and Degunorm™, type IV crown and bridge alloy (CTE= 16.4×10$^{-6}$/° C., 25° C.–500° C.). This system requires rather tedious multistep alloy preparation procedures including a necessary wash bake step prior to application of the opaque; and an excessively long (16–20 min) and complex first dentine bake to assure proper bonding and compatibility of the Duceragold™ porcelain to the Degunorm™ alloy. In particular, the cooling segment (3–4 min between 720° C. and 680° C.) in the first dentine bake is required by the manufacturer to grow additional leucite and may be an indication of instability of leucite in this porcelain. The following Table 2 below sets forth the various properties of the Duceragold™ porcelain.

TABLE 2

| | Duceragold ™ |
| --- | --- |
| Firing Temperature, ° C. | 770–790 |
| Glass Transition Temperature, ° C. | 490 |
| Softening Temperature, ° C. | 595 |
| CTE 25°–600° C., 10$^{-6}$/° C. | 15.8 |
| Recommended alloy | Degunorm |
| Alloy CTE 25°–500° C., 10$^{-6}$/° C. | 16.4 |

U.S. Pat. No. 5,453,290 to Van der Zel is directed to a dental porcelain for use with a dental alloy. The porcelain described therein must be fabricated from three frits, making it more difficult and costly to control the expansion and the glass transition temperature of the final product. Moreover, the CTE of the porcelain must be below the CTE of the alloy by 0.5–1.5 limiting the components to be used together. There is a need to provide a porcelain-fused-to-metal system for dental restorations having simple manufacturing procedures. It is desirable to provide a porcelain that is compatible with alloys of relatively high expansion. It is desireable to provide a two-frit porcelain for use in PFM restorations.

SUMMARY OF THE INVENTION

These and other objects and advantages are accomplished by opaque porcelains for use with metal cores in the manufacture of PFM restorations. The porcelains exhibit a coefficient of thermal expansion (CTE) substantially equal to or slightly above the CTE of the metal to which it is applied. In a preferred embodiment, the porcelains exhibit a CTE equal to or up to about 1.0×10$^{-6}$/° C. higher than the dental alloys to which they are applied as the opaque. The porcelains are fabricated from a mixture of two frit compositions. A high expansion, leucite containing frit is combined with a low fusing glass frit to provide a porcelain having an expansion in the range of 16.9 to about 18.5×10$^{-6}$/° C. in the temperature range of 25°–600° C. By combining two frits, the expansion and fusing temperature can be controlled to the values stated above.

BRIEF DESCRIPTION OF THE DRAWINGS

Features of the present invention are disclosed in the accompanying drawing, wherein.

DESCRIPTION OF THE INVENTION

Figure 1:
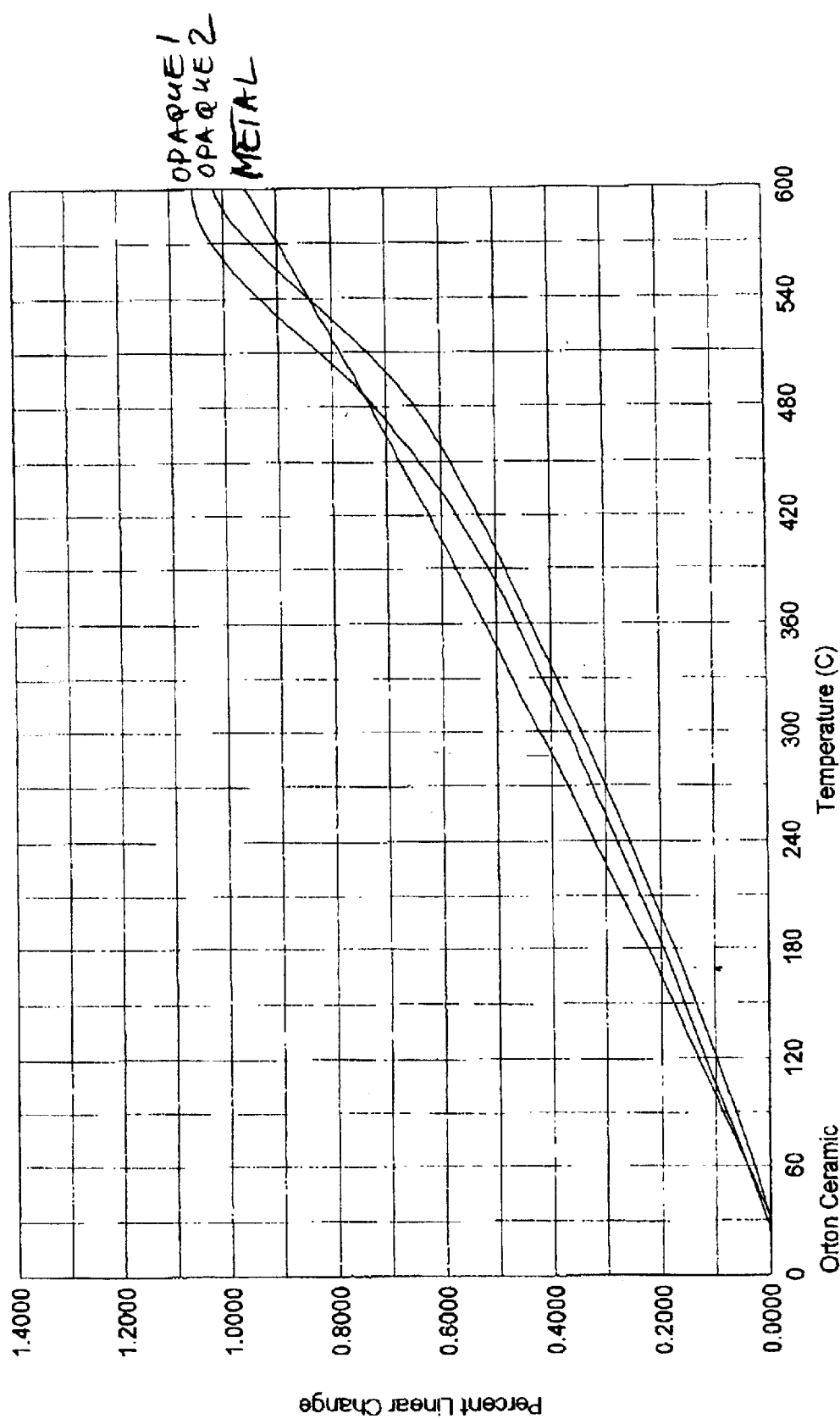
FIG. 1 is dilatometer reading for two opaque compositions and one metal composition.

The invention relates to a porcelain material for use in all-ceramic restorations and PFM restorations. The porcelains exhibit a coefficient of thermal expansion (CTE) substantially equal to or slightly above the CTE of the metal to which it is applied. Preferably, the porcelains exhibit a CTE equal to or up to about 1.5×10$^{-6}$/° C. higher than the dental alloys to which they are applied as the opaque, and more preferably equal to or up to about 1.0×10$^{-6}$/° C. FIG. 1 shows a dilatometer reading of two opaque porcelains herein having different pigment amounts. The two porcelains correspond to Example 6 in Table 7, except that they have different amounts of pigment. Both opaques exhibit higher thermal expansions than the metal after 540° C. Opaque 1 shows a higher thermal expansion than the metal, starting at 480° C. Table 3 below lists the coefficients of thermal expansion for the opaques and metal.

TABLE 3

|  | CTE (25–500° C.) | CTE (25–600° C.) |
|---|---|---|
| Metal | 16.4 | 16.9 |
| Opaque 1 | 16.6 | 18.4 |
| Opaque 2 | 15.0 | 17.8 |

The porcelains herein are compatible with metals having coefficients of thermal expansion (CTE) in the range of from about 15.5 to about $18 \times 10^{-6}/°$ C. in the temperature range from 20° to 600° C. The porcelains exhibit CTEs in the range of about 16.9 to about 18.5 in the temperature range from 20° to 600° C., and preferably in the range of about 17 to about $18 \times 10^{-6}/°$ C. in the temperature range from 20° to 600° C. The porcelains are fabricated from a mixture of two frit compositions. A high expansion, leucite containing frit is combined with a low fusing glass frit to provide a porcelain having an expansion in the range of 16.9 to about $18.5 \times 10^{-6}/°$ C. in the temperature range of 25°–600° C. It is essential to this invention that both the high expansion and the low fusing components of the two-frit mixture exhibit a low glass transition temperature (GTT). It is extremely important that the low fusing component used in the opaque formulation exhibits a GTT lower than about 415° C. By combining two frits, the expansion and firing temperature can be controlled to the values stated above. Opaque porcelains herein having pigments exhibit a coefficient of thermal expansion of average value of about $18 \times 10^{-6}/°$ C. in the temperature range of 25°–600° C. Opaque porcelains without pigments, i.e., white opaques, exhibit coefficients of thermal expansion in the higher end of the range, such as about 17.5 to about $18.5 \times 10^{-6}/°$ C. in the temperature range of 25°–600° C.

Table 4 below shows the compositional ranges of the porcelains for use in the invention.

TABLE 4

| | Body and Incisal Porcelain (by weight percent) | Opaque Porcelain (1) (by weight percent) | Opaque Porcelain (2) (by weight percent) | Opaque Porcelain) (3) (by weight percent) | Opaque Porcelain (4) (by weight percent) |
|---|---|---|---|---|---|
| $SiO_2$ | about 59–about 65 | about 59–about 65 | about 59–about 65 | about 48–about 65 | about 48–about 65 |
| $B_2O_3$ | X | X | X | 0–about 0.7 | 0–about 0.7 |
| $Al_2O_3$ | about 10–about 15 | about 10–about 15 | about 10–about 15 | about 10–about 15 | about 10–about 15 |
| ZnO | X | X | X | 0–about 5 | 0–about 5 |
| CaO | about 0.5–about 2 | about 0.5–about 2 | about 0.5–about 2 | about 0.5–about 2 | about 0.5–about 2 |
| MgO | X | X | X | 0–about 2 | 0–about 2 |
| BaO | X | X | X | 0–about 1 | 0–about 1 |
| $Li_2O$ | about 1.5–about 3 | about 1.5–about 3 | about 1.5–about 3 | about 1.5–about 3 | about 1.5–about 3 |
| $K_2O$ | about 15–about 17 | about 15–about 17 | about 12–about 17 | about 14–about 17 | about 15–about 17 |
| $Na_2O$ | about 4–about 6 | about 4–about 6 | about 4–about 6 | about 4-about 6 | about 4–about 6 |
| $TiO_2$ | X | X | X | 0–about 2 | 0–about 2 |
| $ZrO_2$ | X | X | X | 0–about 17 | 0–about 17 |
| $CeO_2$ | X | X | X | 0–about 1 | 0–about 1 |
| F | about 0.4–about 1 | about 0.4–about 1 | about 0.4–about 1 | about 0.4–about 1 | about 0.4–about 1 |
| $Ta_2O_5$ | — | X | X | 0–about 2 | 0–about 2 |
| $SnO2$ | — | — | — | 0–about 18 | 0–about 18 |
| $ZrSiO_4$ | — | — | — | 0–about 7 | — |
| *Opacifiers | 0–about 1 | about 13–about 20 | about 10–about 20 | — | — |
| **Pigments | 0–about 5 | about 2–about 13 | about 2–about 13 | — | — |

*Opacifiers, $Al_2O_3$, $SnO_2$, $TiO_2$, $ZrO_2$, $ZrSiO_4$, ZnO, $CeO_2$, or $Ta_2O_5$, are admixed as fine powder to a mixture of two frits. The resulting composition is referred to below as White Porcelain (opaque, body or incisal).
**Pigments are admixed as fine powder to a White Porcelain powder. The resulting powder composition is referred to below as Shaded Porcelain (opaque, body or incisal).
X signifies non-essential components.

As set forth in Table 3 above, $Li_2O$, present in an amount of from about 1.5% to about 3%, and F, present in an amount of 0.4%–1%, are instrumental in providing a low glass transition temperature. The presence of $Li_2O$ and F also assist as well in increasing the coefficient of thermal expansion and decreasing the maturing (firing) temperature. The high expansion, leucite containing component of the two-frit mixture has a reasonably low molar ratio of $Al_2O_3$ to the sum of alkali and alkaline earth oxides (R2O+RO). Normally, these compositions are extremely unstable and reactive as well as prone to sanidine precipitation in the temperature range of 650° C.–950° C. It was surprisingly found that certain compositions with specific combinations of $K_2O$, $Na_2O$ and $Li_2O$ are very stable. In addition, it was found that the molar ratio of $Al_2O_3/K_2O$ should be within the range of 0.73–0.95 to assure both the required thermal stability and low glass transition temperature of the high expansion component of the porcelain. The low glass transition temperature provides a porcelain having good compatibility with alloys having CTEs in the range of about 15.5 to about $18 \times 10^{-6}/°$ C. in the temperature range of 25°–600° C. Table 5 below sets forth the properties of the porcelain compositions.

TABLE 5

| PORCELAIN | Body & Incisal | Opaque (1) | Opaque (3) |
|---|---|---|---|
| Firing Temperature/ Maturing Temperature, ° C. | 780–870 | 830–860 | 750–890 |
| Glass Transition Temperature, ° C. | 420–430 | 450–490 | — |
| Softening Temperature, ° C. | 520 | — | — |
| CTE 25°–420° C., $10^{-6}/°$ C. | 15.2 | — | — |
| CTE 25°–500° C., $10^{-6}/°$ C. | 17.2 | 16.0 ± 0.1 | 17–17.5 |
| CTE 25°–600° C., $10^{-6}/°$ C. | — | 18.0 ± 0.5 | — |

Table 6 sets forth compatible alloys for use with the porcelains.

TABLE 6

| Alloy | CTE (25° C.–600° C.) | Application |
|---|---|---|
| Bio-75G ™ alloy | 15.8 | Fast Cool for single units only |
| GoldCore ™ 75 alloy | 16.9 | For single units and bridges |
| GoldCore ™ 55 alloy | 17.35 | For single units and bridges |
| JewelCast ™ alloy | 17.32 | For single units and bridges |
| GoldCore ™ 2 alloy | 17.2 | For single units and bridges |

Table 7 below shows compositional examples of body (incisal) and opaque porcelains.

TABLE 7

| | Example 1 Body/Incisal Porcelain | Comparative Example 1 | Example 2 White Opaque Porcelain for Light* Shades | Example 3 White Opaque Porcelain for Light* Shades | Example 4 White Opaque Porcelain for Dark** Shades | Example 5 White Opaque Porcelain for Dark** Shades | Example 6 White Opaque Porcelain for Light and Dark Shades |
|---|---|---|---|---|---|---|---|
| Two-Frit Mixture Composition | | | | | | | |
| SiO$_2$ | 61.9 | 61.5 | 60.0 | 58.5 | 60.1 | 58.6 | 60.1 |
| B2O3 | 0.5 | 0.5 | 0.6 | 0.6 | 0.6 | 0.6 | 0.6 |
| Al2O3 | 11.6 | 15.4 | 13.6 | 13.6 | 13.7 | 13.6 | 13.1 |
| ZnO | 0.0 | 0.0 | 0.0 | 2.0 | 0.0 | 2.0 | 0.0 |
| CaO | 1.7 | 0.6 | 1.2 | 1.2 | 1.2 | 1.2 | 1.2 |
| MgO | 0.8 | 0.2 | 0.2 | 0.1 | 0.2 | 0.1 | 0.7 |
| BaO | 0.0 | 0.0 | 0.4 | 0.4 | 0.4 | 0.4 | 0.4 |
| Li2O | 2.5 | 2.3 | 2.3 | 2.3 | 2.3 | 2.3 | 2.3 |
| K2O | 15.7 | 12.9 | 15.1 | 15.0 | 15.1 | 15.0 | 15.2 |
| Ta2O5 | 0.0 | 0.0 | 0.0 | 0.0 | 0.0 | 0.0 | 0.0 |
| Na2O | 4.8 | 6.0 | 5.5 | 5.4 | 5.4 | 5.3 | 5.5 |
| TiO2 | 0.0 | 0.0 | 0.0 | 0.0 | 0.0 | 0.0 | 0.0 |
| Zro2 | 0.0 | 0.0 | 0.0 | 0.0 | 0.0 | 0.0 | 0.0 |
| CeO2 | 0.0 | 0.6 | 0.3 | 0.3 | 0.3 | 0.3 | 0.3 |
| F | 0.6 | 0.0 | 0.7 | 0.6 | 0.7 | 0.6 | 0.7 |
| Mixed-In Opacifier | | | | | | | |
| ZrO2 | | | 17 | 17 | 15 | 15 | 17 |
| ZrSiO4 | | | | | | | |
| TiO2 | | | | | | | |
| SnO2 | | | | | | | |
| ZnO | | | | | | | |
| CeO2 | | | | | | | |
| Ta2O5 | | | | | | | |
| Firing temperature | 857 | | 871 | 871 | 871 | 871 | 830–860 |
| CTE (25° C.–500° C.) | 17.2 ± 0.3 | | 17.8 | 17.8 | 17.8 | 17.8 | 16.0 ± 1.0 |
| CTE(25–600° C.° C.) | | | 18 ±0.5 | 18 ±0.5 | 18 ±0.5 | 18 ±0.5 | 18 ± 0.5 |

*Light Opaque Shades - Pigment content < 6 wt %
**Dark Opaque Shades - Pigment content > 6 wt %

The low glass transition temperature of the opaque porcelain is paramount to assure its compatibility with alloys having CTE's in the range of about 15.5 to about 18 (25–600° C.), such as commercially available Gold Core 75™ alloy from Jeneric/Pentron Inc., Wallingford, Conn. This is a gold alloy that does not contain copper and other elements that form dark oxide layers and, therefore, requires much less intricate preparation procedures compared to the Degunorm alloy. Specifically, the Gold Core 75™ alloy forms an adequate oxide layer without compromising the appearance of the coping when degassed at 870° C.–885° C. for about 5–7 min in air or vacuum.

The high potassium content in the porcelain is essential to assure high stability of leucite. High potassium oxide content combined synergetically with other alkali elements (Li and Na) assures as well relatively low glass transition temperature (GTT) and, hence, increased resistance to thermal expansion mismatch cracking and increased adaptability to alloys of slightly lower expansion. It was surprisingly found that increased potassium content increases stability in compositions with low GTT, e.g., Example 1 was found to be much more stable than Comparative Example 1 (compare K$_2$O content). Specifically, dental porcelain of Example 1 has excellent thermal expansion stability and maintains the same thermal expansion after 5 successive bakes at its firing temperature. Dental porcelain of Comparative Example 1 was found to change thermal expansion and opacity upon multiple bakes.

Essential to this invention is that opaque compositions possess a relatively low transition temperature and contain the same elements such as ZnO and Ta$_2$O$_5$ as the oxide layer forming on the alloy that assure good bonding to alloys. Specifically, the oxide layer on the Gold Core 75™ alloy was found to be enriched with ZnO and Ta$_2$O$_5$ and the same components were included in the opaque formulation to improve bonding.

Body and incisal porcelain are typically applied to opaque porcelain, respectively. Preferably, the body and incisal porcelains used with the opaque herein exhibit an average coefficient of thermal expansion of about 17.2.

In a preferred embodiment of the invention, alloys having a CTE in the range of about 15.5 to about 18×10$^{-6}$/° C. in the temperature range of 25°–600° C. are used to manufacture a metal core for a restoration. Opaque porcelains are applied thereto, wherein the CTE is in the range of about 16.9 to about 18.5×10$^{-6}$/° C. in the temperature range of 25°–600° C. and body/incisal porcelains are applied thereto having CTEs in the range of about 16.9 to about 17.7 (from 25°–470 or 500° C.). It is preferred that the opaque porcelain has a CTE about equal to or up to about $1.5 \times 10^{-6}$/° C. higher than the metal core. It is preferred that the body porcelain has a CTE about equal to or up to about $1.5 \times 10^{-6}$/° C. higher than the metal core. It is preferable that the CTE of the opaque is between the CTE of the alloy and the CTE of the body porcelain.

The following examples illustrate the invention.

EXAMPLES

Copings and bridge frameworks cast from Bio-75G, GoldCore75, GoldCore55 and JewelCast alloys available from Jeneric/Pentron, Wallingford, Conn., were prepared with a carbide tool, sand-blasted with alumina sand at pressure of 2 bar and ultrasonically cleaned in water for about 5 min. The same degassing cycle given in the firing charts below was used for Bio-75G, JewelCast, GoldCore55 and GoldCore75 castings. Following degassing, the oxide layer was removed by sand-blasting and castings were ultrasonically cleaned in water for about 5 min. The opaque of the composition of Example 3 (Table 6) was applied in two thin coats and fired according to the firing cycle given in a table below. Body/Incisal porcelain of composition of Example 1 was used to build full contour crowns and bridges and fired up to 5 times as per firing charts below (Tables 8 and 9).

No cracking was observed on single unit restorations made from the alloys above. However, cracks in pontic areas were found when porcelain was fired onto bridge frameworks made from Bio-75G™ alloy. Both single and multi-unit restorations made from GoldCore™ 75, GoldCore™ 55 and JewelCast2™ alloys exhibited no cracking upon multiple firings.

In addition to dental restorations, bond flags were cast from the alloys listed above. Two thin coats of opaque (composition of Example 3) were applied and fired onto the bond flags. Bond flags were bent using pliers and metal surface exposed along the bend where opaque is fractured was inspected using optical stereomicroscope under magnification of 10×. Fracture along opaque-metal interface was found mostly adhesive, i.e. substantial fraction of the metal surface was covered by opaque indicating good bonding between alloys and opaque. The observed coverage was comparable to other metal-porcelain systems and therefore deemed sufficient. Bond strength was quantified according to ISO-9693 Metal-Ceramic Bond Test (Schwickerath crack initiation test). The following Table indicates the bond strengths calculated from the formula $\tau_b = k \cdot F_{fail}$ wherein
  $\tau_b$ is the debonding/crack initiation strength
  k is a coefficient which is a function of the thickness of the metal substrate, and the value of Young's modulus of the used metallic material; and
  $F_{fail}$ is the fracture force

TABLE 8

Firing chart in ° F.

|  | Degassing cycle | Opaque bake (2 coats) | 1st OPC Low Wear bake | 2nd OPC Low Wear bake | 3rd–5th OPC Low Wear bake |
|---|---|---|---|---|---|
| Predry, min | 0 | 6 | 6 | 6 | 6 |
| Low T, ° F. | 1200 | 600 | 1000 | 1000 | 1000 |
| High T, ° F. | 1625 | 1600 | 1575 | 1550 | 1550 |
| Rate, ° C./min | 100 | 75 | 75 | 75 | 75 |
| Vacuum | 100% | 100% | 100% | 100% | 100% |
| VacOn, ° F. | 1200 | 750 | 1000 | 1000 | 1000 |
| VacOff, ° F. | 1625 | 1500 | 1525 | 1500 | 1500 |
| Hold, min | 5 in vacuum | 0 | 0 | 0 | 0 |
| Cool, min | 0 | 0 | 0 | 0 | 0 |

TABLE 9

Firing chart in ° C.

|  | Degassing cycle | Opaque bake (2 coats) | 1st OPC Low Wear bake | 2nd OPC Low Wear bake | 3rd–5th OPC Low Wear bake |
|---|---|---|---|---|---|
| Predry, min | 0 | 6 | 6 | 6 | 6 |
| Low T, ° C. | 650 | 316 | 538 | 538 | 538 |
| High T, ° C. | 885 | 871 | 857 | 843 | 843 |
| Rate, ° C./min | 55 | 42 | 42 | 42 | 42 |
| Vacuum | 100% | 100% | 100% | 100% | 100% |
| VacOn, ° C. | 650 | 399 | 538 | 538 | 538 |
| VacOff, ° C. | 885 | 816 | 829 | 816 | 816 |
| Hold, min | 5 in vacuum | 0 | 0 | 0 | 0 |
| Cool, min | 0 | 0 | 0 | 0 | 0 |

TABLE 10

| Specimen | Thickness (mm) | Elastic Modulus (GPa) | Load (Lbs) | F (fail) Newtons | k | $\tau_b$ (MPa) |
|---|---|---|---|---|---|---|
| gold core 75 | 0.55 | 12.5 | 2.81 | 12.49950291 | 3.6 | 44.99821048 |
| gold core 75 | 0.54 | 12.5 | 2.262 | 10.06187743 | 3.75 | 37.73204037 |
| gold core 75 | 0.55 | 12.5 | 1.81 | 8.051281235 | 3.65 | 29.38717651 |
| gold core 75 | 0.55 | 12.5 | 3.02 | 13.43362946 | 3.65 | 49.03274754 |
| gold core 75 | 0.55 | 12.5 | 2.78 | 12.36605626 | 3.65 | 45.13610535 |
| mean |  |  |  | 0 |  | 41.25725605 |
| Std Dev |  |  |  | 0 |  | 7.791412161 |
| gold core 55 | 0.5 | 15.12 | 1.42 | 6.316474781 | 4.1 | 25.8975466 |
| gold core 55 | 0.5 | 15.12 | 1.07 | 4.759597194 | 4.1 | 19.5143485 |
| gold core 55 | 0.52 | 15.12 | 2.88 | 12.81087843 | 3.8 | 48.68133803 |

TABLE 10-continued

| Specimen | Thickness (mm) | Elastic Modulus (GPa) | Load (Lbs) | F (fail) Newtons | k | $\tau_b$ (MPa) |
|---|---|---|---|---|---|---|
| gold core 55 | 0.5 | 15.12 | 1.68 | 7.473012417 | 4.1 | 30.63935091 |
| gold core 55 | 0.47 | 15.12 | 1.51 | 6.716814732 | 4.7 | 31.56902924 |
| gold core 55 | 0.47 | 15.12 | 0.98 | 4.359257243 | 4.7 | 20.48850904 |
| mean | | | | 0 | | 29.46502039 |
| Std dev | | | | | | 9.724481694 |

As will be appreciated, the present invention provides porcelain compositions compatible with alloys for use in the manufacture of PFM restorations. The porcelains exhibit a coefficient of thermal expansion (CTE) substantially equal to or slightly above the CTE of the metal to which it is applied. The porcelains are fabricated from a mixture of two frit compositions. A high expansion, leucite containing frit is combined with a low melting glass frit to provide a porcelain having an expansion in the range of 16.9 to about $18.5 \times 10^{-6}$/° C. in the temperature range of 25°–600° C. By combining two frits, the expansion and firing temperature can be easily controlled.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A porcelain composition for use as an opaque on dental alloys in the manufacture of a dental restoration comprising by weight percent:
   about 48 to about 65% $SiO_2$;
   about 10 to about 15% $Al_2O_3$;
   about 0.5 to about 2% CaO;
   about 1.5 to about 3% $Li_2O$;
   about 15 to about 17% $K_2O$;
   about 4 to about 6% $Na_2O$; and
   about 0.4 to about 1 F;
   wherein the porcelain possesses a coefficient of thermal expansion of about 16.9 to about 18.5 in the temperature range of 25° C. to 600° C.

2. The porcelain of claim 1 wherein the coefficient of thermal expansion is slightly higher than the dental alloys to which it is applied as the opaque.

3. The porcelain of claim 2 wherein the coefficient of thermal expansion is equal to or up to about $1.5 \times 10^{-6}$/° C. higher than the dental alloys to which it is applied as the opaque in the temperature range of 25° C. to 600° C.

4. The porcelain composition of claim 1 possessing a coefficient of thermal expansion which is compatible with alloys possessing a coefficient of thermal expansion in the range of about 15.5 to about $18 \times 10^{-6}$/° C. in the temperature range of 25°–600° C.

5. The composition of claim 1 further comprising by weight:
   about 0 to about 0.7% $B_2O_3$;
   about 0 to about 5% ZnO;
   about 0 to about 2% MgO;
   about 0 to about 1% BaO;
   about 0 to about 2% $TiO_2$;
   about 0 to about 17% $ZrO_2$;
   about 0 to about 7% $ZrSiO_4$;
   about 0 to about 1% $CeO_2$;
   about 0 to about 2% $Ta_2O_5$; and
   about 0 to about 18% $SnO_2$.

6. A method of making a dental restoration comprising:
   forming a dental porcelain powder from a dental composition comprising about 48 to about 65% $SiO_2$, about 10 to about 15% $Al_2O_3$, about 0.5 to about 2% CaO, about 1.5 to about 3% $Li_2O$, about 14 to about 17% $K_2O$, about 4 to about 6% $Na_2O$, and about 0.4 to about 1 F, wherein the maturing temperature is in the range of about 750° C. to about 890° C.;
   shaping the dental porcelain powder onto a metal core; and
   heating the shaped dental porcelain powder to between about 750° C. to about 880° C. to fuse the dental porcelain powder to the metal core;
   wherein the metal core exhibits a coefficient of thermal expansion in the range from about 15.5 to about $18 \times 10^{-6}$/° C. (measured from 25° C. to 600° C.).

7. The method of claim 6 wherein the metal framework comprises a gold alloy.

8. The method of claim 6 wherein the porcelain powder is an opaque porcelain.

9. The method of claim 8 further comprising applying a body porcelain over the opaque porcelain.

10. The method of claim 9 further comprising applying an incisal porcelain over the body porcelain.

11. The method of claim 10 wherein the incisal porcelain comprises:
    about 59 to about 65% $SiO_2$;
    about 10 to about 15% $Al_2O_3$;
    about 0.5 to about 2% CaO;
    about 1.5 to about 3% $Li_2O$;
    about 15 to about 17% $K_2O$;
    about 4 to about 6% $Na_2O$; and
    about 0.4 to about 1 F.

12. The method of claim 11 wherein the incisal porcelain comprises a mixture of a high expansion leucite-containing frit and a low fusing glass frit.

13. The method of claim 12 wherein the incisal porcelain comprises a mixture of frits.

14. The method of claim 9 wherein the body porcelain comprises:
    about 59 to about 65% $SiO_2$;
    about 10 to about 15% $Al_2O_3$;
    about 0.5 to about 2% CaO;
    about 1.5 to about 3% $Li_2O$;
    about 15 to about 17% $K_2O$;
    about 4 to about 6% $Na_2O$; and
    about 0.4 to about 1 F.

15. A porcelain composition comprising by weight percent:
- about 59 to about 65% $SiO_2$;
- about 10 to about 15% $Al_2O_3$;
- about 0.5 to about 2% CaO;
- about 1.5 to about 3% $Li_2O$;
- about 15 to about 17% $K_2O$;
- about 4 to about 6% $Na_2O$; and
- about 0.4 to about 1 F.
- about 10 to about 20% of an opacifier;
- wherein the porcelain composition is used as an opaque in the manufacture of dental restorations and possesses a coefficient of thermal expansion of about 16.9 to about 18.5 in the temperature range of 25° C. to 600° C.

16. The porcelain composition of claim 15 wherein the opacifier is selected from $Al_2O_3$, ZnO, $TiO_2$, $ZrO_2$, $ZrSiO_4$, $CeO_2$, $Ta_2O_5$, $SnO_2$ and mixtures thereof.

17. The porcelain composition of claim 15 wherein it is applied to dental alloys and wherein the coefficient of thermal expansion is equal to or up to about $1.5 \times 10^{-6}$/° C. higher than the dental alloys to which it is applied as the opaque in the temperature range of 25° C. to 600° C.

18. A dental restoration comprising:
- a metal core, having a coefficient of thermal expansion below about $18 \times 10^{-6}$/° C. (measured from 25° C. to 600° C.); and
- an opaque porcelain applied on the metal core, having a coefficient of thermal expansion (measured from 25° C. to 600° C.) about equal to or up to about $1.5 \times 10^{-6}$/° C. higher than the metal core;
- wherein the opaque porcelain comprises about 48 to about 65% $SiO_2$; about 10 to about 15% $Al_2O_3$; about 0.5 to about 2% CaO; about 1.5 to about 3% $Li_2O$; about 15 to about 17% $K_2O$; about 4 to about 6% $Na_2O$; and about 0.4 to about 1 F.

19. The dental restoration of claim 18 wherein the opaque porcelain further comprises:
- about 0 to about 0.7% $B_2O_3$;
- about 0 to about 5% ZnO;
- about 0 to about 2% MgO;
- about 0 to about 1% BaO;
- about 0 to about 2% $TiO_2$;
- about 0 to about 17% $ZrO_2$;
- about 0 to about 7% $ZrSiO_4$;
- about 0 to about 1% $CeO_2$;
- about 0 to about 2% $Ta_2O_5$; and
- about 0 to about 18% $SnO_2$.

20. A dental restoration comprising:
- a metal core, having a coefficient of thermal expansion below about $18 \times 10^{-6}$/° C. (measured from 25° C. to 600° C.);
- an opaque porcelain applied on the metal core, having a coefficient of thermal expansion (measured from 25° C. to 600° C.) about equal to or up to about $1.5 \times 10^{-6}$/° C. higher than the metal core; and
- a body porcelain applied to the opaque porcelain having a coefficient of thermal expansion (measured from 25° C. to 600° C.) about equal to or up to about $1.5 \times 10^{-6}$/° C. higher than the metal core.

21. The dental restoration of claim 20 wherein the coefficient of thermal expansion of the opaque porcelain is between the coefficient of thermal expansion of the alloy and the coefficient of thermal expansion of the body porcelain.

22. A dental restoration comprising:
- a metal core, having a coefficient of thermal expansion below about $18 \times 10^{-6}$/° C. (measured from 25° C. to 600° C.); and
- an opaque porcelain applied on the metal core, having a coefficient of thermal expansion (measured from 25° C. to 600° C.) about equal to or up to about $1.5 \times 10^{-6}$/° C. higher than the metal core;
- wherein the opaque porcelain comprises about 59 to about 65% $SiO_2$; about 10 to about 15% $Al_2O_3$; about 0.5 to about 2% CaO; about 1.5 to about 3% $Li_2O$; about 12 to about 17% $K_2O$; about 4 to about 6% $Na_2O$; and about 0.4 to about 1 F.

23. A method of making a dental restoration comprising:
- forming a dental porcelain powder from a dental composition comprising about 59 to about 65% $SiO_2$; about 10 to about 15% $Al_2O_3$; about 0.5 to about 2% CaO; about 1.5 to about 3% $Li_2O$; about 12 to about 17% $K_2O$; about 4 to about 6% $Na_2O$; and about 0.4 to about 1 F, wherein the maturing temperature is in the range of about 750° C. to about 890° C.;
- shaping the dental porcelain powder onto a metal core; and
- heating the shaped dental porcelain powder to between about 750° C. to about 880° C. to fuse the dental porcelain powder to the metal core;
- wherein the metal core exhibits a coefficient of thermal expansion in the range from about 15.5 to about $18 \times 10^{-6}$/° C. (measured from 25° C. to 600° C.).

* * * * *